United States Patent [19]

Gonzalez, Jr. et al.

[11] Patent Number: 5,080,897
[45] Date of Patent: Jan. 14, 1992

[54] NOVEL BACILLUS THURINGIENSIS STRAINS, AND RELATED INSECTICIDAL COMPOSITIONS

[75] Inventors: Jose M. Gonzalez, Jr., W. Trenton; Anthony Macaluso, Lawrence, both of N.J.

[73] Assignee: Ecogen Inc., Langhorne, Pa.

[21] Appl. No.: 185,613

[22] Filed: Apr. 25, 1988

Related U.S. Application Data

[63] Continuation-in-part of Ser. No. 47,965, May 8, 1987, abandoned.

[51] Int. Cl.$^5$ .......................... C12N 1/12; C12P 21/00; A61K 37/00
[52] U.S. Cl. .................................. 424/93; 435/252.5; 435/252.31; 435/172.3; 935/74; 935/56
[58] Field of Search ............ 424/93; 435/172.3, 172.1, 435/252.3, 252.31, 320.1; 935/64, 74

[56] References Cited

U.S. PATENT DOCUMENTS

1,479,279  1/1989  Karamata et al. .................... 424/93

FOREIGN PATENT DOCUMENTS

178151    4/1986  European Pat. Off. ....... 435/252.31
2221024   5/1987  European Pat. Off. ......... 435/172.3

OTHER PUBLICATIONS

Aronson et al., Microbiol. Rev. (1986) 50:1-24.
Chapman et al., 1985, "Conjugal Plasmid Transfer in Bacillus Thuringiensis", in Plasmids in Bacteria, Helinski et al., ed., Plenum Publish. Corp. (1985), pp. 453-467.
Carlton et al., 1985, in D. Dubnau, ed., The Molecular Biology of the Bacilli, vol. II, Academic Press (1985), pp. 211-249.
Carlton et al., 1985, "Plasmids and Delta-Endotoxin Production in Different Subspecies of Bacillus thuringiensis", in Molecular Biology of Microbial Differentiation, Hoch, ed., Am. Soc. Microb. (1985) pp. 246-252.
Gonzalez, Jr., 1984, "Genetic Analysis of the Toxin Plasmids of Bacillus Thuringiensis", Ph.D. Thesis, University of Georgia, pp. 112-154.
Gonzalez, Jr. et al., Plasmid (1984) 11:28-38.
Klier et al., Mol. Gen. Genet. (1983) 191:257-262.
Kronstad et al., J. Bacteriol. (1983) 154:419-428.
Ward et al., FEBS Lett. (1983) 158:45-49.
Gonzalez, Jr. et al., Proc. Natl. Acad. Sci. U.S.A. (1982) 79:6951-6955.
Gonzalez et al., 1982, "Plasmid Transfer in Bacillus thurgiensis", in Genetic Exchange, Streips et al., ed., Marcel Dekker, Inc. (1982) pp. 85-95.
Gonzalez et al., Plasmid (1981) 5:351-365.
Minnich et al., "Regulation of Protoxin Synthesis in Bacillus thuringiensis", J. Bacteriol. 158:447-454 (1984).

*Primary Examiner*—Robin L. Teskin
*Attorney, Agent, or Firm*—Christopher Egolf

[57] ABSTRACT

The present invention relates to novel *Bacillus thuringiensis* transconjugant strains having improved insecticidal activity. The novel strains are produced by a combination of plasmid curing and conjugation of active strains.

9 Claims, 5 Drawing Sheets

: CONJUGATION IN LIQUID BROTH

NOVEL BACILLUS THURINGIENSIS STRAINS, AND RELATED INSECTICIDAL COMPOSITIONS

This application is a continuation-in-part of Ser. No. 07/047,965 filed May 8, 1987 now abandoned.

TABLE OF CONTENTS

1. Introduction
2. Background of the Invention
   2.1. Commercial Pesticides: General Considerations
   2.2. Biological Pesticides
   2.3. *Bacillus thuringiensis* and Delta-Endotoxins
3. Summary of Invention
4. Brief Description of the Figures
Description of the Invention
   5.1. Curing of *B. thuringiensis* and Conjugation
   5.2. Isolation of HD-1 Variants
   5.3. Isolation of HD269-2 (EG2069)
   5.4. Isolation of HD263-4 (EG2038)
   5.5. Isolation of HD263-4-1 (EG2094)
   5.6. Isolation of HD263-4-5A (EG2101)
   5.7. Isolation of HD269-2-7 (EG2348)
   5.8. Isolation of HD269-2-30 (EG2371)
   5.9. Isolation of HD279-72 (EG2157)
   5.10. Isolation of HD269-2-8 (EG2349)
   5.11. Isolation of HD1-19-8 (EG2397)
   5.12. Summary of Isolation and Construction of Novel BT Strains
   5.13. Products and Formulations Incorporating BT Strains
6. Bioassays
   6.1. Bioassay of HD-1 Variants
   6.2. Bioassay of BT Strain HD269-2-30
   6.3. Bioassay of BT Strain HD269-2-7
   6.4. Bioassay of BT Strain HD269-2
   6.5. Bioassay of BT Strains HD1-19-8, HD279-72, and HD269-2-8
7. Deposit of Microorganisms

1. INTRODUCTION

This invention relates to new strains of *Bacillus thuringiensis* and a method for their isolation, identification and improvement. These new strains have enhanced activity against lepidopteran pests. This invention also relates to insecticidal compositions incorporating these novel strains.

2. BACKGROUND OF THE INVENTION

2.1. COMMERCIAL PESTICIDES: GENERAL CONSIDERATIONS

Each year, significant portions of the world's commercially important agricultural crops are lost to insects and other pest infestation. The damage wrought by these pests extends to all areas of commercially important plants including foods, textiles, and various domestic plants, and the economic damage runs well into the millions of dollars. Thus, protection of crops from such infestations is of paramount concern.

Broad spectrum pesticides are most commonly used for crop protection, but indiscriminate use of these agents can lead to disruption of the plant's natural defensive agents. Furthermore, because of their broad spectrum of activity, the chemical pesticides may destroy non-target organisms such as beneficial insects and parasites of destructive pests. These are also frequently toxic to animals and humans, and thus, pose environmental hazards when applied.

Additionally, insects and other organisms have frequently developed resistance to these pesticides when repeatedly exposed to them. In addition to reducing the utility of the pesticide, resistant strains of minor pests may become major infestation problems due to the reduction of beneficial parasitic organisms.

This is a major problem encountered in using broad spectrum pesticides. What is needed is a biodegradable pesticide that combines a narrower spectrum of activity with an ability of maintaining its activity over an extended period of time, i.e., to which resistance develops much more slowly, or not at all. Biopesticides appear to be useful in this regard.

2.2. BIOLOGICAL PESTICIDES

Biopesticides, also called biorationals, make use of naturally occurring pathogens (diseases) to control insect, fungal, and weed infestations of agricultural crops. Such substances comprise a bacterium which produces a substance toxic to the infesting agent (a toxin), with or without a bacterial growth medium. Such bacteria can be applied directly to the plants by standard methods of application, and are typically less harmful to non-target organisms and the environment as a whole, in comparison to chemical pesticides.

The use of biological methods of pest control was first suggested in 1895 when a fungal disease was discovered in silkworms. It was not until 1940, however, when spores of the milky disease bacterium *Bacillus popilliae* applications were used to control the Japanese beetle, that successful biological pest control was first achieved. A bacterium named *Bacillus thuringiensis* (BT) that makes a toxin fatal to caterpillars is currently the most widely used biopesticide. In the late 1960's, the discovery of HD-1, a highly toxic strain of BT, set the stage for commercial use of biopesticides.

2 3. *Bacillus thuringiensis* AND DELTA-ENDOTOXINS

*Bacillus thuringiensis* (otherwise known as "B.t." or "BT") is a widely distributed, rod shaped, aerobic and spore forming microorganism. During its sporulation cycle BT forms proteins known as protoxins or delta-endotoxins. These protoxins are deposited in BT as parasporal, crystalline inclusions or as part of the spore coat. The pathogenicity of BT to a variety of sensitive insects, such as those in the orders Lepidoptera and Diptera, is essentially due to this parasporal crystal, which may represent over 20% of the dry weight of the BT cell at the time of sporulation.

The parasporal crystal is active in the insect only after ingestion. For instance, after ingestion by a lepidopteran insect, the alkaline pH and proteolytic enzymes in the mid-gut activate the crystal allowing the release of the toxic components. These toxic components poison the mid-gut cells causing the insect to cease feeding and eventually to die. In fact, BT has proven to be an effective and environmentally safe insecticide in dealing with lepidopteran pests.

It has been reported that different strains of BT produce serologically different parasporal crystals. However, one of the predominant crystal forms, of bipyramidal shape, produced by many of the BT strains is composed of a protein(s) known as P1. P1 proteins have a molecular weight of about 130,000 daltons (d) and may also be present in the spore coat. The genes for the parasporal crystal P1, and those of most of the other protein crystals, reside on one or more of a large number of plasmids of varying size in BT.

3. SUMMARY OF INVENTION

This invention provides for biologically pure strains of *Bacillus thuringiensis* which have insecticidal activity against insects of the order Lepidoptera. These strains have been derived by both plasmid curing and conjugation procedures.

It is also an object of this invention to provide a novel method for recognizing the plasmid containing the gene coding for a toxin protein in a BT strain and, thereby, enable the selective use of specific strains of BT for plasmid curing and conjugation experiments so as to derive a strain of BT having specific or enhanced insecticidal activity.

It is further an object of this invention to provide a method for controlling insects in the order Lepidoptera with these novel *Bacillus thuringiensis* strains. All of the above embodiments of this invention will be described in greater detail in the description of the invention which follows.

4. BRIEF DESCRIPTION OF THE FIGURES

FIG. 3 is a flow chart illustrating the construction of novel BT strains described in §5.1–5.8. In the drawing, "spont." means the BT variant arose spontaneously; "Δ" means the BT variant was isolated after growth at high temperature; "L.D.E." means linear DNA elements; and "D", "R" and "T" mean donor, recipient and transconjugant, respectively.

FIG. 5 is a flow chart illustrating the construction of novel BT strains described in §5.9–5.11. In the drawing, "spont." means the BT variant arose spontaneously; "Δ" means the BT variant was isolated after growth at high temperature; "L.D.E." means linear DNA elements; and "D", "R" and "T" mean donor, recipient and transconjugant, respectively.

5. DESCRIPTION OF THE INVENTION

Generally stated, the present invention provides novel *Bacillus thuringiensis* strains which have insecticidal activity against insects of the order Lepidoptera. Biologically pure cultures of these strains have been deposited with the NRRL. Bioassays described below have confirmed the activity of these strains. These strains of BT, therefore, are preferred for use as at least one of the active ingredients in an insecticidal composition useful against lepidopteran, dipteran, or coleopteran insects.

Essentially this invention comprises combining and optimizing several techniques (e.g., isolation of new BT strains, curing and transfer of toxin plasmids, use of isogenic strains, plasmid array analysis, assigning specific toxicities to individual toxin plasmids), so as to achieve a novel systematic approach of modifying B.t. strains for greater toxicity to any given susceptible insect.

Generally stated, this invention provides a method for producing a *Bacillus thuringiensis* having selective insecticidal activity against insects comprising:

(a) providing a first *Bacillus thuringiensis* strain, having a specific insecticidal activity conferred by a gene coding for an insecticidal toxin protein, said gene being located on a plasmid, in admixture with an intermediate Bacillus recipient strain whereby said intermediate Bacillus recipient strain acquires by conjugation the plasmid conferring insecticidal activity;

(b) isolating and identifying said intermediate Bacillus recipient strain which has acquired said plasmid conferring insecticidal activity;

(c) providing the transconjugant intermediate Bacillus recipient strain isolated in step (b) in admixture with a second *Bacillus thuringiensis* strain whereby said second *Bacillus thuringiensis* strain acquires the plasmid conferring insecticidal activity from said transconjugant intermediate Bacillus recipient strain and (d) isolating and identifying a transconjugant from the culture admixture of step (c), having selectively targeted insecticidal activity.

The method above also encompasses the embodiment wherein the transconjugant of step (d) produces increased amounts of insecticidal toxin over the said second *Bacillus thuringiensis* strain.

The method above additionally encompasses the embodiment wherein identification of the transconjugants in steps (b) and (d) is by visualization of the plasmid arrays of the intermediate Bacillus recipient strain and the second *Bacillus thuringiensis*.

For instance, in a preferred embodiment of this invention a first *Bacillus thuringiensis* strain having, for example, lepidopteran activity, is provided in admixture first with a second *Bacillus thuringiensis* strain (or *B. cereus*) whereby said second *Bacillus thuringiensis* strain acquires (by conjugation) the plasmid conferring insecticidal activity against Lepidoptera. The strain which acquired the toxin encoding plasmid is identified by methods such as gel electrophoresis to determine its plasmid array which would show plasmids acquired, besides those known to exist in that second strain); isolating the strain which acquired the toxin plasmid and then providing that transconjugant strain in admixture with a third *Bacillus thuringiensis* having a selective insecticidal activity (i.e. to different lepidopteran insects or to diptera or coleoptera) under conditions favoring conjugation whereby said third *Bacillus thuringiensis* strain having activity acquires the plasmid conferring insecticidal activity by conjugation from said transconjugant strain. The resultant BT strain may, therefore, have a wider range of selective activity against different species of lepidopteran pests (each of which have varying degrees of sensitivity to a particular BT toxin), or against lepidopteran and dipteran insects, lepidopteran and coleopteran, or dipteran and coleopteran pests. The new BT strains of this invention may serve as an inexhaustible source of toxin plasmids of greater specificity and toxicity, which can then be transferred by conjugation into any of several recipient strains to generate novel strains with previously unknown combinations of toxin plasmids and toxin proteins.

This invention also provides for novel insecticides for use against Lepidoptera, Coleoptera, or Diptera comprising a mixture of BT and a suitable carrier. The BT strain or strains may be used in the form of spores, whole organisms, or a combination of these. A suitable carrier may be any one of a number of solids or liquids known to those of skill in the art.

All of these aspects of the invention are described below in detail and are illustrated in the following examples.

5.1. CURING OF B. THURINGIENSIS AND CONJUGATION

Insecticidal strains of *Bacillus thuringiensis* (BT) are distinguished from the related species *B. cereus* by their production of a proteinaceous inclusion, the parasporal crystal, during sporulation. The protein(s) that make up the crystal(s) determine the toxicity of the individual BT strain (that is, whether lepidopteran, dipteran, or coleopteran larvae are affected). The genes encoding the proteins of the toxin crystals are located on extrachromosomal DNA molecules (plasmids). BT strains making large amounts of toxin crystal protein have been shown by various technical approaches to contain two or more distinct toxin plasmids. Each toxin plasmid in a strain codes for its own toxin protein(s), which can often be distinguished from the toxin protein(s) encoded by the other toxin plasmid(s) present, by immunological, electrophoretic, or other technical means.

Curing is the loss of plasmid DNA. Curing of one or more toxin plasmids (in a multiple toxin plasmid BT strain), and possibly even non-toxic plasmids, may lead to increased production of toxin protein(s) encoded by the remaining toxin plasmid(s). If the remaining toxin plasmid or plasmids encode a more potent toxin than did the lost toxin plasmid or plasmids, the toxicity of the derived, partially-cured strain will be greater on a protein basis, and sometimes also on a raw (dosage) basis. Thus, by curing a BT strain of specific plasmids, the type of toxin protein that it synthesizes may be altered to give greater toxicity against a given target insect. This can mean that the toxin derivative would be more specific against that insect.

Curing of plasmids may be achieved by number of different methods. Plasmid curing does occur spontaneously at a low level, and these spontaneously cured strains may be detected by routine screening. However, curing can also be actively induced, by elevation of the culture temperature. This is preferably done in steps, i.e., progressively brought up from about 37° C. up to about 45° C. Exposure of the strains to detergents, such as sodiumdodecyl sulfate or chemicals which interfere with DNA replication, such as acridines, ethidium bromide, or novobiocin, may also be used to increase the frequency of plasmid curing. For the present purposes, elevated temperature is generally preferred. BT toxin plasmids of a medium size range (about 40 to 90 megadaltons (Md)) can usually transfer from the strain that carries them into other BT or *B. cereus* strains. If the recipient strain is crystal-negative (Cry−), acquisition of a toxin plasmid converts it to crystal production (Cry+). This method is known as conjugative plasmid transfer and is one way of identifying a plasmid as a toxin plasmid. It has also been used to determine the toxicity and specificity of individual toxin plasmids, by comparing their toxin product(s) in an isogenic background. Transconjugants (i.e. which originally may have been isogenic strains) carrying a single toxin plasmid can be used as donors in turn, and strains already carrying one or more toxin plasmids can be used as recipients, and can acquire additional toxin plasmids as described in Section 5.0 above and in Sections 5.6, 5.7, 5.8, 5.10 and 5.11 below)

5.2. ISOLATION OF HD-1 VARIANTS

HD-1, a BT strain of variety kurstaki (flagellar serotype 3ab) is the BT strain most frequently used in the U.S. to control lepidopteran pests. HD-1 was subjected to extensive curing manipulations in an effort to improve its specificity and activity against caterpillar pests attacking cotton plants, especially the two Heliothis sps., *H. virescens* hereinafter referred to as HV, and *H. zea* hereinafter referred to as HZ. A group of HD-1 variants altered in plasmid content, either missing one or more plasmids (e.g., partially cured), or having more complex changes in their plasmid array, was generated and bioassayed against HV and HZ.

Loss of individual plasmids showed that HD1-1 (the wild-type strain) contained two toxin plasmids, 44 and 115 Md in size. The 115-Md plasmid coded for two types of toxin protein crystal: a bipyramidal crystal, known as P1, containing proteins about 130,000 d in size, and a flattened cuboidal crystal, known as P2, composed of protein(s) 68,000 d in size. The 115-Md plasmid contains at least two distinct P1 toxin genes, known as the 4.5 and 6.6 genes. The 44-Md toxin plasmid coded for a P1-type protein, distinct from those coded by the 115-Md plasmid, being slightly smaller in size by approximately 2000 d.

The gene coding for this slightly smaller P1 protein is known as a 5.3-type gene. Cultures of HD-1 variants lacking the 44-Md toxin plasmid made bipyramidal (P1) crystals smaller than those made by HD-1 variants carrying both toxin plasmids (and therefore containing a larger number of P1 genes). On the other hand such strains made P2 crystals which were noticeably larger than those in strains carrying the smaller P1 toxin plasmid. Therefore, strains carrying only one toxin plasmid, the 115-Md, made larger quantities of P2 toxin, and had greater ratios of P2 vs. P1 produced. Electrophoresis of the crystals from a large group of HD-1 variants confirmed the microscopic observation of the increasing size of the P2.

Figure 1:
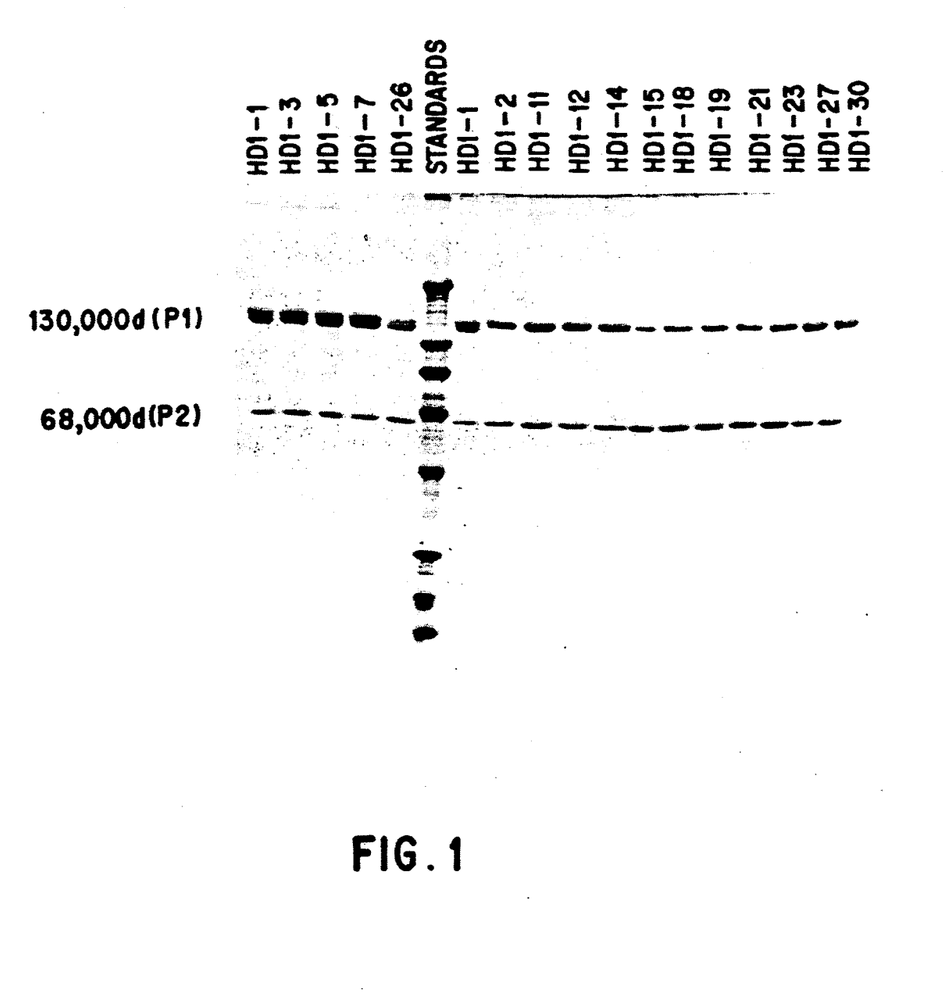
FIG. 1 is a photograph of a gel electrophoresis of solubilized crystals from HD1-1 and several derived strains, which shows differential production of P1 and P2 crystal proteins in the various strains.

In FIG. 1, toxin proteins from strains carrying both toxin plasmids (HD1-1, -3, -5, -7, -26) or the 115-Md plasmid only (HD1-2, -11, -12, -14, -27, -30) have been electrophoresed and resolved according to size. Equal amounts of cultures, grown under identical conditions, were loaded on the gel. The strains carrying only the 115-Md toxin plasmid show an approximately 50% reduction in the intensity of the P1 band, reflecting the loss of the P1 toxin gene(s) on the 44-Md plasmid. The P2 protein band, however, showed a 50-100% rise in intensity, caused by the increase in yield of P2 protein in these strains.

Some of the derivatives in FIG. 1 had undergone more radical alterations than plasmid curing; in HD1-15, -8, -19, -21, and -23, the 44-Md plasmid was lost, and then one of the P1 toxin genes (the "6.6" gene) on the 115-Md plasmid was spontaneously deleted, so that these derivatives have only two active toxin genes, a 4.5-type P1 gene and a P2 gene. Microscopic observation, confirmed by the gel in FIG. 1, show that cells of this strain produce P1 and P2 proteins in roughly equal amounts.

5.3. ISOLATION OF HD269-2 (EG2069)

The BT strain HD-269 was obtained from the U.S.-D.A. as a mixed culture of two closely-related variants. The existence of these variants was unknown at the time of receipt of the culture. Both of these variants were isolated, characterized (as with the HD-1 variants) and established as a biologically pure culture. One variant, HD269-1 (EG2068) contained two toxin plasmids, of sizes 110 Md and 69 Md. The other variant, HD269-2 (EG2069), was a partially-cured derivative of HD269-1 and lacked the 69-Md toxin plasmid.

5.4. ISOLATION OF HD263-4 (EG2038)

The HD-263 parental strain, HD263-1 (EG2035), contains three toxin plasmids of sizes 110 Md, 60 Md, and 44 Md. HD263-1 was grown with shaking in Difco nutrient broth at an elevated temperature (42° C.) overnight, then single colonies were isolated from the overnight culture. A colony that had lost the 44-Md toxin plasmid was discovered by random screening of single colonies on agarose gels, to detect the absence of the 44-Md plasmid, and named HD263-4.

5.5. ISOLATION OF HD263-4-1 (EG2094)

The BT strain HD1-9 (EG2009) (see TABLE IV) was used as a donor by growing it together with recipient strain HD73-26 in nutrient salts broth. Nutrient salts broth consists of 0.8% Difco nutrient broth supplemented with $Mg^{++}$ (to 1 mM), $Ca^{++}$ (to 0.7 mM) and $Mn^{++}$ (to 0.05 mM). Plasmid transfer was carried out by inoculating spores of donor and recipient strains into nutrient salts broth and allowing the strains to grow together for 31 hours at 30° C., with gentle shaking. Afterwards, colonies of the recipient strain were selected by using streptomycin-containing plates (HD73-26 is resistant to streptomycin) and Cry+ colonies were then identified by phase contrast microscopy. In this manner, the transconjugant HD73-26-4 (EG2236) was created, which acquired the 44+ Md transmissible P1-toxin coding plasmid from HD1-9. HD73-26-4 was then used as a donor by inoculating its spores and those of the recipient strain HD263-4 (EG2038) together into liquid M27 broth (the recipe is given in Section 6.1) and growing them together at 30° C. for 7 hours with gentle shaking. The transconjugant HD263-4-1 (EG2094), which had acquired the 44+ Md P1 toxin plasmid from HD73-26-4, was isolated by random screening of recipient-type (P1P2+) colonies on agarose gels.

5.6. ISOLATION OF HD263-4-5A (EG2101)

The BT strain HD-122A (EG2175) was used as a donor by growing it together with recipient strain HD73-26 by inoculating spores of both strains into M27 broth (composition described in Section 6.1 below) and allowing the strains to grow together for 8 hours at 30° C., with gentle shaking. Afterwards, colonies of the recipient strain were selected by using streptomycin-containing plates (HD73-26 is resistant to streptomycin) and Cry+ colonies were then identified by phase contrast microscopy. In this manner, the transconjugant HD73-26-23 (EG2255) was created, which acquired the 46+ and 5.4 Md plasmids from HD-122A. HD73-26-23 was then used as a donor by inoculating its spores and those of the recipient strain HD263-4 (EG2038) together into M27 broth and growing them together at 30° C. for 8 hours with gentle shaking. The transconjugant HD263-4-5A (EG2101), which had acquired the 46+ Md P1 toxin plasmid from HD73-26-23, was isolated by random screening of recipient-type (P1P2+) colonies on agarose gels.

5.7. ISOLATION OF HD269-2-7 (EG2348)

The BT strain HD-122A (EG2175) was used as a donor by growing it together with recipient strain HD73-26 by inoculating spores of both strains into M27 broth and growing them together for 8 or more hours at 30° C., with gentle shaking. Afterwards, colonies of the recipient strain were selected by using streptomycin-containing plates (HD73-26 is resistant to streptomycin) and Cry+ colonies were then identified by phase contrast microscopy. In this manner, the transconjugant HD73-26-23 (EG2255) was created, which acquired the 46+ and 5.4 Md plasmids from HD-122A. HD73-26-23 was then used as a donor by inoculating its spores and those of the recipient strain HD269-2 (EG2069) together into M27 broth and growing them together at 30° C. for 16 hours with gentle shaking. The transconjugant HD269-2-7 (EG2348), which had acquired the 46+ Md P1 toxin plasmid from HD73-26-23, was isolated by random screening of recipient-type (P1P2+) colonies on agarose gels.

5.8. ISOLATION OF HD269-2-30 (EG2371)

The BT strain EG2461, isolated from grain dust, was used as a donor by growing it together with recipient strain HD73-26 by inoculating spores of both strains into M27 broth and growing them together for 9½ hours at 30° C., with gentle shaking. Afterwards, colonies of the recipient strain were selected by using streptomycin-containing plates (HD73-26 is resistant to streptomycin) and then $Cry^+$ colonies were identified by phase contrast microscopy. In this manner, the transconjugant HD73-26-67 (EG2299) was created, which acquired the L.D.E. and 47+ Md plasmid from EG2461. HD73-26-67 was then used as a donor by inoculating its spores and those of the recipient strain HD269-2 (EG2069) together into M27 broth and growing them together at 30° C. for 68 hours with gentle shaking. The transconjugant HD269-2-30 (EG2371), which had acquired the L.D.E. and 47+ Md P1 toxin plasmid from HD73-26-67, was isolated by random screening of recipient-type (P1P2+) colonies or agarose gels.

5.9. ISOLATION OF HD279-72 (EG2157)

The HD-279 parental strain, HD279-1 (EG2154), contains three toxin plasmids of sizes 110 Md, 60 Md, and 44 Md. HD279-1 was grown on Luria Agar (1% Peptone, 0.5% Yeast Extract, 0.5% NaCl, 1.2% agar) at an elevated temperature (43° C.) for several days, then colonies derived from single cells were isolated from the overgrown colony. A colony that had lost the 60-Md toxin plasmid was discovered by random screening of single colonies on agarose gels and named HD279-72 (EG2157).

5.10. ISOLATION OF HD269-2-8 (EG2349)

The BT strain HD-232B (EG2167) was used as a donor by growing it together with recipient strain HD73-26. Spores of both strains were inoculated into M27 broth and grown together for 8 or more hours at 30° C., with gentle shaking. Afterwards, colonies of the recipient strain were selected by using streptomycin-containing plates (HD73-26 is resistant to streptomycin) and $Cry^+$ colonies were then identified by phase contrast microscopy. In this manner, the transconjugant HD73-26-25 (EG2257) was created, which acquired the 50+, L.D.E., 9.6, 5.4, and 1.4 Md plasmids from HD-232B. HD73-26-25 was then used as a donor by inoculating its spores and those of the recipient strain HD269-2 (EG2069) together into M27 broth and growing them together at 30° C. for 16 hours with gentle shaking. The transconjugant HD269-2-8 (EG2349), which had acquired the 50+ Md P1 toxin plasmid, and also the 9.6 Md and 1.4 Md plasmids and L.D.E. from HD73-26-25, and had lost the 7.5 Md plasmid native to HD269-2, was isolated by random screening of recipient-type (P1P2+) colonies on agarose gels.

5.11. ISOLATION OF HD1-19-8 (EG2397)

The BT strain HD-137A (EG2161) was used as a donor by growing it together with recipient strain HD73-26. Spores of both strains were inoculated into M27 broth and grown together for 8 or more hours at 30° C., with gentle shaking. Afterwards, colonies of the recipient strain were selected by using streptomycin-containing plates (HD73-26 is resistant to streptomycin) and Cry+ colonies were then identified by phase contrast microscopy. In this manner, the transconjugant HD73-26-34 (EG2266) was created which acquired the 42+ Md plasmids from HD-137A. HD73-26-34 was then used as a donor by inoculating its spores and those of the recipient strain HD1-19 (EG2019) together into M27 broth and growing them together at 30° C. for 7 hours with gentle shaking. The transconjugant HD1-19-8 (EG2397), which had acquired the 42+ Md P1 toxin plasmid from HD73-26-34, was isolated by random screening of recipient-type (P1P2+) colonies on agarose gels.

5.12. SUMMARY OF ISOLATION AND CONSTRUCTION OF NOVEL BT STRAINS

The origins and plasmid contents of several strains related to this invention, including partially-cured and transconjugant derivatives of HD-263 and HD-269, are described in TABLE I, some of which strains are deposited at the NRRL.

TABLE I

HD73-1 (EG2180): Prototype strain, var. kurstaki, from France.
  Plasmids: 50, 50, 7.5, 5.4, 5.2, 4.9 Md
  Toxin plasmid: 50 (P1)
HD73-26 (EG2205): Derived from prototype strain HD73-1 by loss of 50, 50, 7.5, 5.4 and 5.2 Md plasmids and addition of streptomycin resistance.
  Plasmids: 4.9 Md
  Toxin plasmids: None (crystal-negative)
HD263-1 (EG2035): Prototype strain, var. kurstaki, from England.
  Plasmids: 130, 110, 60, 44, 43, 7.5, 5.4, 5.2, 5.0, 4.9, 1.4 Md.
  Toxin plasmids: 110 (pl, p2), 60 (P1), 44 (P1)
HD263-4 (EG2038): Strain HD263-1 cured of the 44-Md toxin plasmid.
  Toxin plasmids: 110 (P1 , P2), 60 (P1)
HD263-4-1 (EG2094): Transconjugant using HD263-4 as recipient that has acquired the 44-Md (P1) toxin plasmid of HD-1.
HD263-4-5A (EG2101): Transconjugant using HD263-4 as recipient that has acquired the 46 Md (P1) toxin plasmid of HD-122A.
HD269-1 (EG2068): Prototype strain from England, var. kurstaki.
  Plasmids: 130, 110, 69, 49, 44, 7.5, 5.4, 5.2, 5.0 and 4.9 Md
  Toxin plasmids: 110 (P1 , P2) 69 (P1)
HD269-2 (EG2069): Derived from HD269-1 by spontaneous loss of the 69 Md toxin plasmid.
HD269-2-7 (EG2348): Transconjugant using HD269-2 as recipient that has acquired the 46 (P1) Md toxin plasmid from HD-122A.
HD269-2-30 (EG2371): Transconjugant using HD269-2 as recipient that has acquired the 47 Md (P1) toxin plasmid from EG2461.
HD1-1 (EG2001): Prototype strain, var. kurstaki, from USA. Plasmids: 130, 115, 53, 51, 44, 29, 9.6, 5.4, 5.2, 4.9, 1.4 Md and L.D.E.
  Toxin plasmids: 115 (P1,P2), 44 (P1)
HD1-9 (EG2009): Derived from prototype strain HD1-1 (USA) by loss of 130, 115, 51, 9.6, and 5.4 Md plasmids and the L.D.E.
  Plasmids: 53, 44, 29, 5.2, 4.9, 1.4 Md
  Toxin plasmid: 44 (P1)
HD-122A (EG2175): Prototype strain probably from England, var. aizawai.
  Plasmids: 120, 110, 78, 50, 46, 43, 33, 31, 6.0 (O.C.), 8.0, 5.4, 4.7, 3.5 Md and L.D.E.
  Toxin plasmids: 110 (P1), 46(P1)
EG2461: Novel BT isolated from Kansas, U.S.A. grain dust sample (wheat).
  Plasmids: 120, 110, 47, 44, 34, L.D.E, 6.0 (OC), 8.2, 8.0, 7.2, 7.0, and 3.5 Md
  Toxin plasmid: 110 (P1), 47 (P1)
HD279-72 (EG2157): Derived from HD279-1 by loss of the 60 Md toxin plasmid.
HD73-26-25(EG2257): Transconjugant using HD73-26 as recipient that has acquired the 50+ (P1), 9.6, 5.4, 1.4 Md plasmids and L.D.E. from HD-232B (EG2167).
HD269-2-8 (EG2349): Transconjugant using HD269-2 (EG2069) as recipient that has acquired the 50+ (P1), 9.6, and 1.4 plasmids, and L.D.E. from HD73-26-25 (EG2257), and host the 7.5 Md plasmid.
HD73-26-34 (EG2266): Transconjugant using HD73-26 as recipient that has acquired the 42+ Md (P1) toxin plasmid from HD-137A (EG2161).
HD1-19-8 (EG2397): Transconjugant using HD1-19 (EG2019) as recipient which has acquired the 42+ Md (P1) toxin plasmid from HD73-26-34 (EG2266).
"L.D.E." is a linear DNA element, approx. 10 Md in size. "OC" indicates plasmid DNA exists chiefly as open circles. "_" indicates plasmid is a toxin plasmid.

Figure 2:
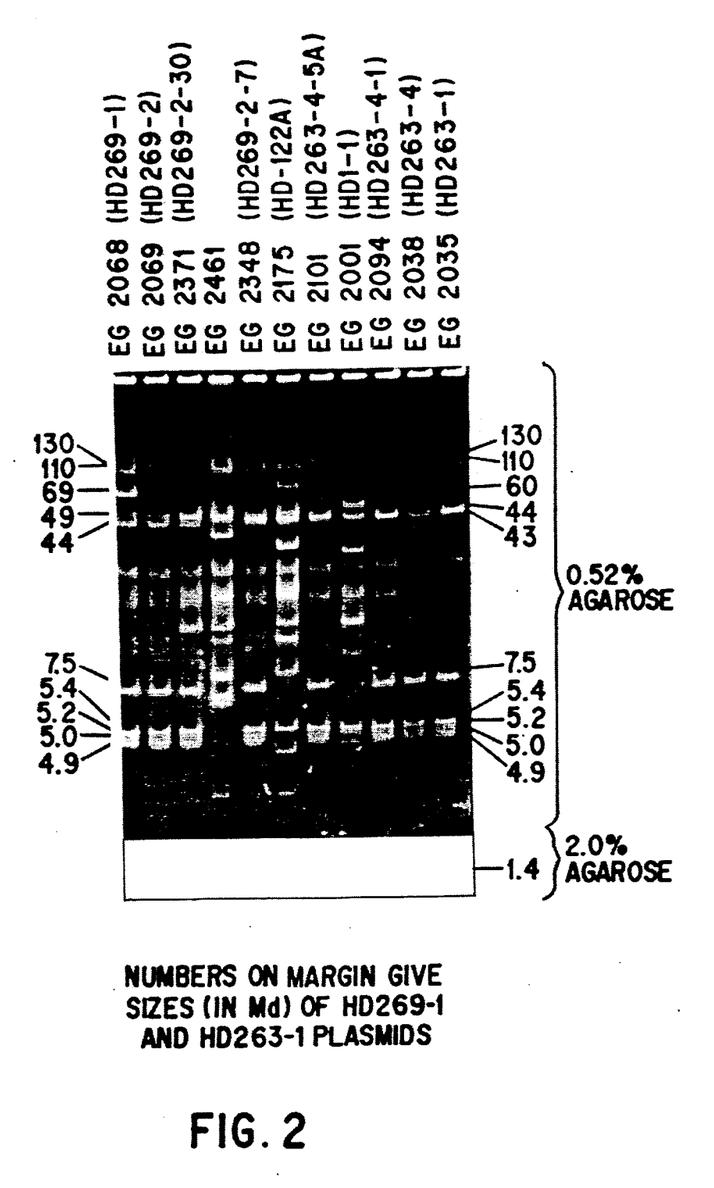
FIG. 2 is a photograph of a gel electrophoresis which shows the plasmid arrays of the novel BT strains deposited with the NRRL and also BT strains used as donors and recipients, as described in §5.1–5.8, and constructed as illustrated in FIG. 3.
Figure 3:
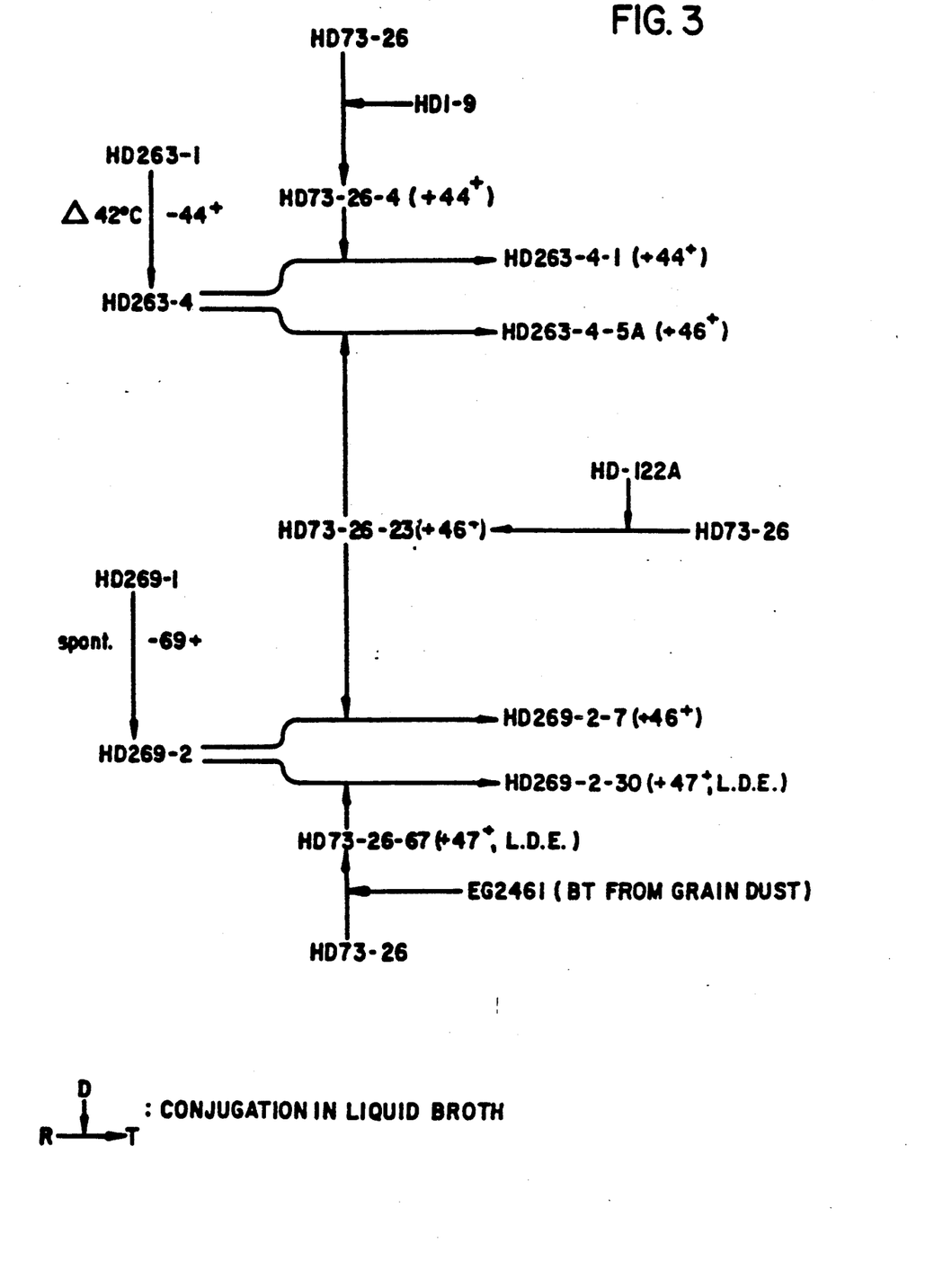
Figure 4:
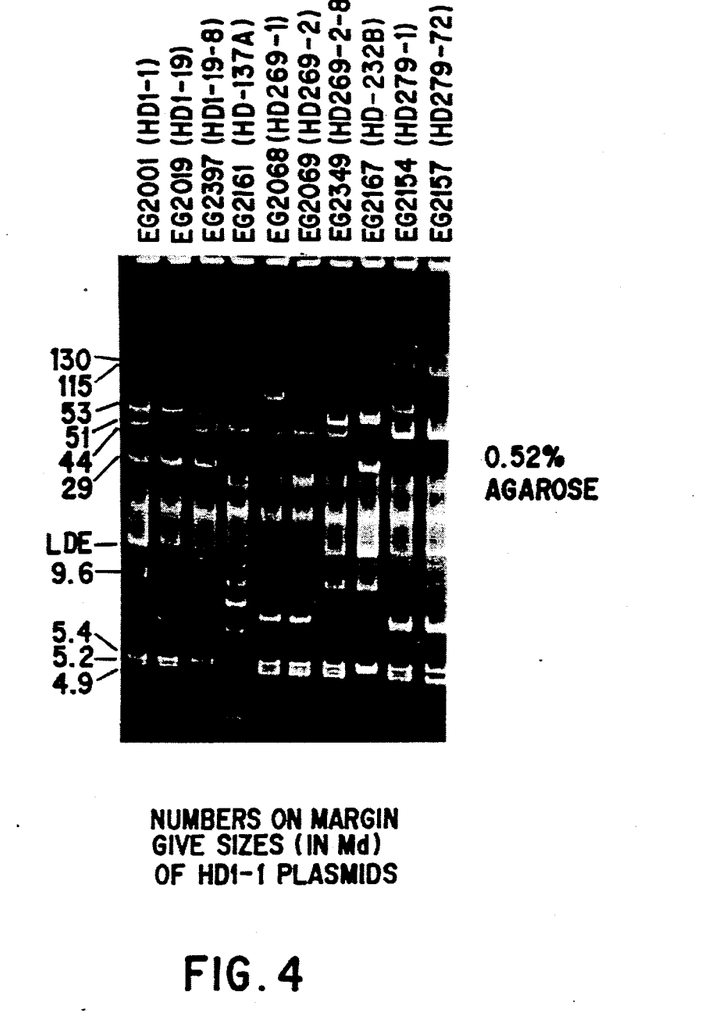
FIG. 4 is a photograph of a gel electrophoresis which shows the plasmid arrays of novel BT deposited with the NRRL, as well as BT strains used as donors and recipients, as described in §§5.9–5.11, and constructed as illustrated in FIG. 5.
Figure 5:
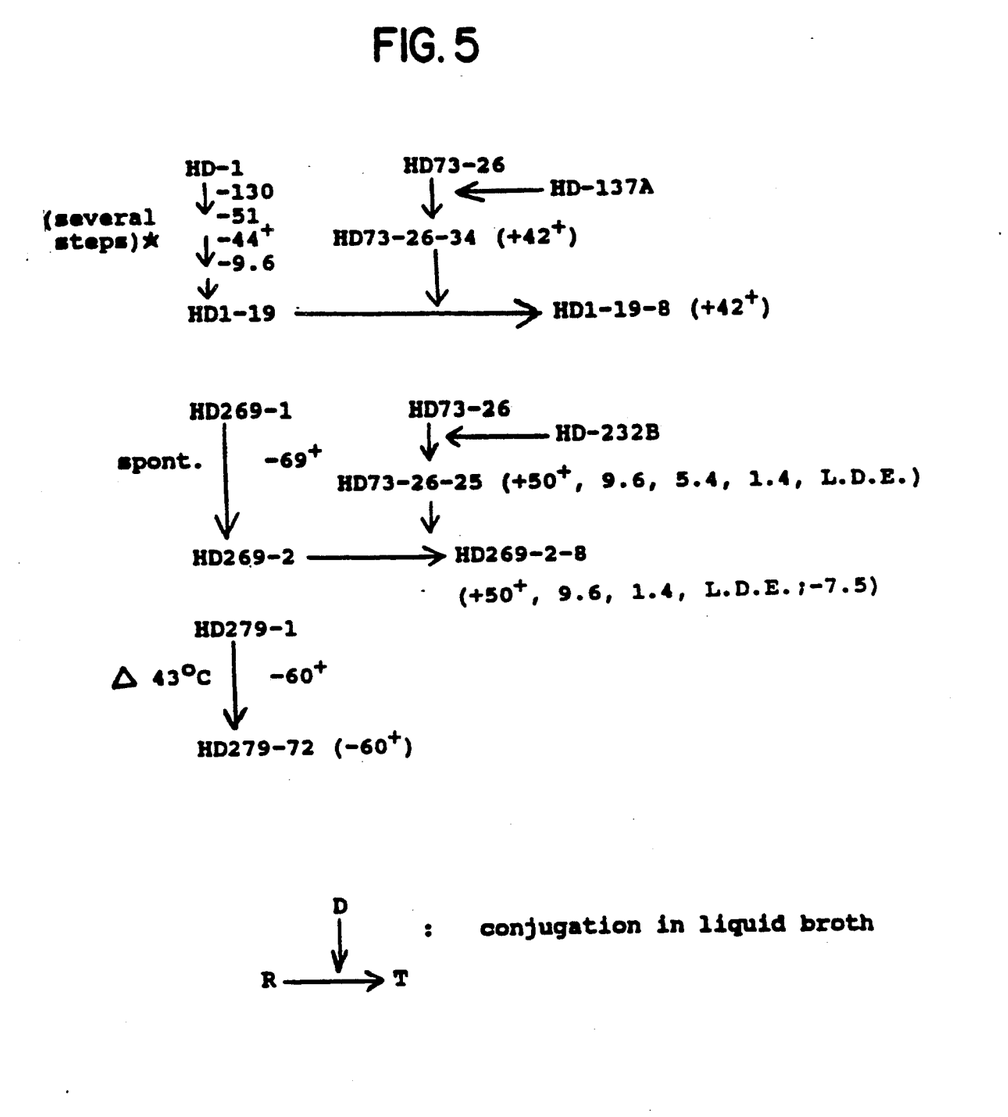

The plasmid arrays of the novel BT strains deposited at the NRRL and those of the main precursors used in their isolation, are shown on the gel in FIG. 2 and 4. The pathways of construction of the novel BT strains of this invention as described in Sections 5.3-5.11 are summarized in FIGS. 3 and 5.

5.13. PRODUCTS AND FORMULATIONS INCORPORATING BT STRAINS

BT may be used as a potent insecticidal compound with activity against lepidopteran, dipteran, and coleopteran insects. It is, therefore, within the scope of the invention that these BT strains be utilized as an insecticide((the active ingredient) alone, or as part of a mixture of BT with other microorganisms. The compositions of this invention containing these strains of BT are applied at an insecticidally effective amount which will vary depending on such factors as, for example, the specific insects to be controlled, the specific plant to be treated and method of applying the insecticidally active compositions. The preferred insecticide formulations are made by mixing BT, alone or with another organism, with the desired carrier. The formulations may be administered as a dust or as a suspension in oil (vegetable or mineral) or water, a wettable powder or in any other material suitable for agricultural application, using the appropriate carrier adjuvants. Suitable carriers can be solid or liquid and correspond to the substances ordinarily employed in formulation technology, e.g., natural or regenerated mineral substances, solvents, dispersants, wetting agents, tackifiers, binders or fertilizers.

The compositions of the invention containing BT are applied to the appropriate insect habitat at an insecticidally effective amount which, as noted above, will vary depending on such factors as, for example, the specific insects to be controlled, the specific plant to be treated and the method of applying the insecticidally active compositions.

Target crops (i.e., potential habitats for Lepidoptera, Diptera, and Coleoptera) protected by the present invention comprise, but are not limited to, the following species of plants: cereals (such as wheat, barley, corn, rye, oats, rice, sorghum, and related crops), beets, cotton, leguminous plants, oil plants (such as poppy, olives, and sunflowers) cucumber plants, fiber plants, citrus fruit, vegetables (such as lettuce), deciduous trees and conifers.

Generally stated, the preferred compositions usually contain 0.1 to 99%, preferably 0.1 to 95%, of the insecticidal microorganism *Bacillus thuringiensis*, or combination thereof, with other active ingredients, 1 to 99.9% of a solid or liquid adjuvant, and 0 to 25%, preferably 0.1 to 20%, of a surfactant.

The formulations containing a solid or liquid adjuvant, are prepared in known manner, e.g., by homogeneously mixing and/or grinding the active ingredients with extenders, e.g., solvents, solid carriers, and in some cases surface active compounds (surfactants).

Suitable liquid carriers are vegetable oils, such as coconut oil or soybean oil, mineral oils or water. The solid carriers used, e.g., for dusts and dispersible powders, are normally natural mineral fibers such as calcite, talcum, kaolin, or attapulgite. In order to improve the physical properties it is also possible to add highly dispersed silicic acid or highly dispersed absorptive carriers of porous types, for example pumice, broken brick, sepiolite or bentonite. Suitable nonsorbent carriers are materials such as silicate or sand. In addition, a great number of pregranulated materials or inorganic or organic mixtures can be used, e.g., especially dolomite or pulverized plant residues.

Depending on the nature of the active ingredients to be formulated, suitable surface-active compounds are non-ionic, cationic and/or anionic surfactants having good emulsifying, dispersing and wetting properties. The term "surfactants" will also be understood as comprising mixtures or surfactants.

Suitable anionic surfactants can be both water-soluble soaps and water-soluble synthetic surface active compounds.

Suitable soaps are the alkali metal salts, alkaline earth metal salts or unsubstituted ammonium salts of higher fatty acids ($C_{10}$-$C_{20}$), e.g. the sodium or potassium salts of oleic or stearic acid, or natural fatty acid mixtures which can be obtained, e.g., from coconut oil or tallow oil., Further stable surfactants are also the fatty acid methyllaurin salts as well as modified and unmodified phospholipids.

More frequently, however, so-called synthetic surfactants are of use, especially fatty sulfonates, fatty sulfates, sulfonated benzimidazole derivatives or alkylarylsulfonates.

The fatty sulfonates or sulfates are usually in the forms of alkali metal salts, alkaline earth metal salts or unsubstituted ammonium salts and generally contain a $C_6$-$C_{22}$ alkyl, e.g., the sodium or calcium salt of dodecylsulfate, or of a mixture of fatty alcohol sulfate, obtained from fatty acids. These compounds also comprise the salts of sulfonic acid esters and sulfonic acids of fatty alcohol/ethylene oxide adducts. The sulfonated benzimidazole derivatives preferably contain two sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g., salts of the phosphoric acid ester of an adduct of p-nonylphenol with 4 to 14 moles of ethylene oxide.

Nonionic surfactants are preferably polyglycol ether derivative or aliphatic or cycloaliphatic alcohol or saturated or unsaturated fatty acids and alkylphenols, said derivative containing 3 to 10 glycol ether groups and 8 to 20 carbon atoms in the (aliphatic) hydrocarbon moiety and 6 to 18 carbon atoms in the alkyl moiety of the alkylphenols.

Other suitable non-ionic surfactants are the water soluble adducts of polyethylene oxide with alkylpropylene glycol, ethylenediaminopolypropylene glycol and alkylpolypropylene glycol contain 1 to 10 carbon atoms in the alkyl chain, which adducts contain 20 to 250 ethylene glycol ether groups and 10 to 1000 propylene glycol ether groups.

Representative examples of non-ionic surfactants are nonylphenolpolyethanols, castor oil, glycol ethers, polypropylene/polyethylene oxide adducts, tributylphenoxypoly ethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as substituents on the nitrogen, at least one $C_8$-$C_{22}$ alkyl radical and, as further substituents, lower unsubstituted or halogenated alkyl bensyl, or hydroxylated lower alkyl radicals. The salts are preferably in the form of halides, methyl sulfates or ethylsulfates, e.g., stearyltrimethylammonium chloride.

6 BIOASSAYS

Bioassays are conducted by topically applying a known amount of BT suspension containing a known weight of BT powder to the surface of an artificial agar-based diet. The diet is contained in a plastic cup and is uniform in surface area from cup to cup. Multiple cups are treated at each treatment dose. After the liquid carrier has evaporated, one newly hatched larva is placed in each cup, the cup is then capped, and the assay is incubated for 7 days at 30 degrees (centigrade) at which time mortality is recorded. The LC50 value is determined via a computer program which converts the dose-mortality data to probits and calculates the lethal concentration at which 50% of the test population would die. The protein LC50 or PLC50 is calculated by multiplying the LC50 value of the sample by the percent of that sample which is crystal protein as determined by a chemical assay.

A stock suspension of the BT sample is prepared by weighing 20-30 mg of the powder into a glass screw cap vial and adding 20 ml of 0.005% Triton X-100, The suspension is then sonicated for about 15 seconds.

Bioassays generally consist of a series of 8 doses with each subsequent dose being ½ or ⅔ of the previous dose. Thirty insects are usually tested at each dose. The stock suspension is used to inoculate the tube containing the highest dose. A dilution series is then conducted. One-hundred microliters of the appropriate suspension is placed on the surface of each diet cup for that dose. The liquid is spread evenly over the diet surface and after evaporation the test insect is placed on the diet surface.

The BT powder may be prepared according to the following sequential procedure.

1. Centrifuge final broth or Pellicon concentrate in 500 ml centrifuge bottles for 20 minutes at 7000 rpm (in JA-10 rotor). (NB. Adjust pH of broth to 7.0 prior to centrifuging).
2. Remove and discard supernatant.
3. Resuspend pellet in minimal amount of deionized water. Stir on magnetic stirrer for 10 minutes until homogeneous slurry is obtained.
4. Add 4–5 volumes of acetone.
5. Stir acetone suspension for 30 minutes.
6. Centrifuge suspension for 10 minutes at 7500 rpm (JA-10 rotor).
7. Discard supernatant and resuspend pellet in approx. 100 ml acetone.
8. Stir to resuspend pellet (approx. 10 minutes or until an even slurry is obtained).
9. Filter slurry through Whatman #1 filter paper.
10. Repeat steps 7–9.
11. Transfer final powder to aluminum weigh boat and allow to dry overnight.
12. Weigh final powder for yield and transfer to 60 ml polypropylene bottle for storage at 4° C.

6.1. BIOASSAY OF HD-1 VARIANTS

The HD-1 variants were grown for bioassay as follows: spores were inoculated into 5 mls of M27 broth in a 50 ml sterile flask. M27 broth is composed of 33 mM each of $HPO_4$= and $H_2PO_4$-anions; 98 mM $K^+$; 0.17% peptone; 0.1% beef extract; 150 mM NaCl; 5.5 mM glucose; 330 μM $Mg^{++}$, 230 μM $Ca^{++}$, and 17 μM $Mn^{++}$ (added as the chloride salts). The cultures were incubated at 30° C. with shaking for 3 days, at which time sporulation and crystal formation were complete. Five μl of sterile 1-octanol were added as an anti-foaming agent and the cultures were vortexed to generate a homogeneous suspension, transferred to sterile plastic tubes, sealed, and stored at 5° C.

Bioassay of these liquid cultures on larvae of three species of lepidopterans revealed that different HD-1 variants had significantly different toxicities, as shown in TABLE II.

TABLE II

TOXICITIES OF HD-1 DERIVATIVES AGAINST DIFFERENT SPECIES OF LEPIDOPTERANS

| | Toxicity (PLC50) against | | |
|---|---|---|---|
| | HZ | TN | SE |
| HD1-1 | 182 | 156 | 146 |
| HD1-2 | 107 | 78 | 165 |
| HD1-12 | 104 | 117 | 157 |
| HD1-19 | 105 | NA | 116 |

HZ = *H. zea*; TN = *T. ni*; SE = *S. exigua*; NA = not available)
(PLC50 is in ng of preparation/600 $mm^2$ of diet surface.)

HD-1 derivatives such as HD1-12 were used as recipients in conjugative matings, during which the recipient strain cells would acquire new toxin plasmids from the donor strain. In this way, transconjugants of HD1-12 were obtained that contained both the 115-Md native toxin plasmid of HD1-12, and one or more toxin plasmids originating in other strains of BT. It was hoped that some of these transconjugant strains, harboring novel combinations of toxin plasmids, would make toxin crystals of improved toxicity relative to those of HD1-1 (the original, parental strain), measured on a protein basis as lethal concentration per nanogram (ng) of toxin protein. This in fact, turned out to be the case as shown in TABLE III.

TABLE III

VARIATIONS IN TOXICITY OF HD1-12 TRANSCONJUGANTS IN WHICH THE 44-MD TOXIN PLASMID IS REPLACED BY A TOXIN PLASMID FROM ANOTHER BT STRAIN

| | PLC50 | |
|---|---|---|
| Strain | HV | HZ |
| HD1-1 (wild type) | 20 | 140 |
| HD1-12-9 | 6 | 142 |
| HD1-12-10 | 17 | 107 |
| HD1-12-11 | 25 | 109 |
| HD1-12-12 | 23 | 91 |
| HD1-12-13 | 14 | 90 |
| HD1-12-14 | 7 | 49 |
| HD1-12-15 | 17 | 85 |
| HD1-12-16 | 21 | 92 |
| HD1-12-17 | 21 | 113 |
| HD1-12-18 | 23 | 161 |
| HD1-12-19 | 10 | 135 |
| HD1-12-20 | 9 | 204 |

(PLC50 is in ng of preparation/600 $mm^2$ of diet surface)

Table III lists the $PLC_{50}$ (concentration of toxin protein killing 50% of the test insects) on HV and HZ of 12 transconjugants of HD1-12, HD1-12-9 through HD1-12-20, each of which carries a different new toxin plasmid (from 12 different donor strains). Against HV, the toxicities range from a little worse than HD1-1 (HD1-12-11) to over three times as toxic as HD1-1 (HD1-12-9). Against HZ, these transconjugants ranged from not as toxic as HD1-1 (HD1-12-20) to over twice as toxic (HD1-12-14). There are two important conclusions that may be drawn from these data. A BT strain can be improved (or made worse) against a given insect by plasmid curing and/or plasmid acquisition. In addition, a certain degree of targeting is possible; of the 12 transconjugants presented in TABLE III, HD1-12-9 is highly toxic against HV but no better than HD1-1 against HZ. Conversely, some of the transconjugants (such as HD1-12-15) were better than HD1-1 against HZ, but no better than HD1-1 against HV.

Results comparable to those obtained with HD1-1, its variants and transconjugants, have also been obtained with BT strain HD269, that originally contained two or more toxin plasmids. Some of these results are presented in TABLE IV.

TABLE IV

CHANGES IN ACTIVITY OF TOXIN PROTEIN (IN PLC50) OF BT STRAIN HD-269 THROUGH PLASMID CURING AND PLASMID TRANSFER

| Strain | Comment | Insect | PLC$_{50}$ |
|---|---|---|---|
| HD269-1 | Wild type | SE | 193 |
| HD269-2 | Cured of one toxin plasmid | SE | 115 |
| HD269 2 | Cured of one toxin plasmid | HV | 11 |
| HD269-2-1 | Cured of one toxin plasmid; acquired new tox. plas. | HV | 4 |
| HD269-2 | Cured of one toxin plasmid | HZ | 103 |
| HD269-2-1 | Cured of one toxin plasmid; acquired new tox. plas. | HZ | 40 |

PLC50 is in ng of preparation/600 mm$^2$ of diet surface

6.2. BIOASSAY OF BT STRAIN HD269-2-30

Bioassays of BT strain HD269-2-30 were carried out and in §6.1 utilizing two different powder formulations. The results are set forth below in Tables V and VI.

TABLE V

BT Strain HD269-2-30

| Insect | PLC50 |
|---|---|
| ON | 3.2 |
| HV | 2.5 |
| HZ | 13.2 |
| HZ | 9.9 |
| SE | 37.9 |
| SE | 45.5 |
| TN | 15.2 |
| TN | 26.3 |

Insects
ON = Ostrinia nubilalis European cornborer
HV = Heliothis virescens Tobacco budworm
HZ = Heliothis zea Bollworm or corn earworm
SE = Spodoptera exigua Beet armyworm
TN = Trichoplusia ni Cabbage looper
PLC50 is in ng of preparation/600 mm$^2$ of diet surface

TABLE VI

BT strain HD269-2-30

| Insect | PLC50 |
|---|---|
| HV | 4.9 |
| HZ | 47.1 |
| HZ | 58.4 |
| SE | 62.6 |
| SE | 108.8 |
| TN | 24.5 |
| TN | 11.8 |

HV = Heliothis virescens Tobacco budworm
HZ = Heliothis zea Bollworm or corn earworm
SE = Spodoptera exigua Beet armyworm
TN = Trichoplusia ni Cabbage looper
PLC50 is in nanograms of preparation/600 mm$^2$ of diet surface These results indicate that BT strain HD269-2-30 has varying degrees of activity against different lepidopteran insects.

6.3 BIOASSAY OF BT STRAIN HD269-2-7

A bioassay of BT strain HD269-2-7 was carried out generally according to the procedure set forth above in §6.0 and in §6.1 utilizing two different powder preparations. The results are set forth below in TABLES VII AND VIII.

TABLE VII

BT STRAIN HD269-2-7

| Insect | PLC50 |
|---|---|
| LD | 3.2 |
| LD | 8.0 |
| HV | 2.1 |
| HV | 1.1 |

TABLE VII-continued

BT STRAIN HD269-2-7

| Insect | PLC50 |
|---|---|
| HV | 4.0 |
| HZ | 15.1 |
| HZ | 13.0 |
| SE | 45.1 |
| TN | 13.0 |

Insects
LD = Lymantria dispar Gypsy moth
HV = Heliothis virescens Tobacco budworm
HZ = Heliothis zea Bollworm or corn earworm
SE = Spodoptera exigua Beet armyworm
TN = Trichoplusia ni Cabbage looper
PLC50 is in nanograms of preparation/600 mm$^2$ of diet surface.

TABLE VIII

BT STRAIN HD269-2-7

| Insect | PLC50 |
|---|---|
| LD | 2.8 |
| HV | 4.0 |
| HV | 3.3 |
| HV | 4.3 |
| HZ | 30.6 |
| HZ | 28.9 |
| SE | 46.0 |
| SE | 66.0 |
| SE | 52.0 |
| TN | 10.5 |
| TN | 12.3 |

Insects
LD = Lymantria dispar Gypsy moth
HV = Heliothis virescens Tobacco budworm
HZ = Heliothis zea Bollworm or corn earworm
SE = Spodoptera exigua Beet armyworm
TN = Trichoplusia ni Cabbage looper
PLC50 is in nanograms of preparation/600 mm$^2$ of diet surface.

These results indicate that BT strain HD269-2-7 has varying degrees of activity against different lepidopteran insects.

6.4. BIOASSAY OF BT STRAIN HD269-2

A bioassay of BT strain 269-2 was carried out generally according to the procedure set forth above in §6.0 an in §6.1, utilizing two different powder preparations. The results are set forth below in TABLES IX AND X.

TABLE IX

BT STRAIN HD269-2

| Insect | PLC50 |
|---|---|
| HV | 1.7 |
| HV | 1.7 |
| HZ | 8.3 |
| HZ | 16.4 |
| HZ | 9.7 |
| SE | 25.7 |
| SE | 39.4 |
| SE | 57.7 |

Insects
HV = Heliothis virescens Tobacco budworm
HZ = Heliothis zea Bollworm or corn earworm
SE = Spodoptera exigua Beet armyworm
PLC50 is in nanograms of preparation/600 mm$^2$ of diet surface.

TABLE X

BT STRAIN HD269-2

| Insect | PLC50 |
|---|---|
| HV | 1.3 |
| HZ | 9.4 |
| HZ | 18.3 |
| SE | 94.0 |
| SE | 88.0 |
| TN | 15.7 |

TABLE X-continued

| BT STRAIN HD269-2 | |
| --- | --- |
| Insect | PLC50 |
| LD | 15.7 |

Insects
LD = *Lymantria dispar* Gypsy moth
HV = *Heliothis virescens* Tobacco budworm
HZ = *Heliothis zea* Bollworm or corn earworm
SE = *Spodoptera exigua* Beet armyworm
TN = *Trichoplusia ni* Cabbage looper
PLC$_{50}$ is in nanograms of preparation/600 mm$^2$ of diet surface.

These results indicate that BT strain 269-2 has varying degrees of activity against different lepidopteran insects.

6.5. 269-2 BIOASSAY OF BT STRAINS HD1-19-8, HD279-72, AND HD269-2-8

A bioassay of the novel strains HD1-19-8, HD279-72 and HD269-2-9 was carried out generally according to the procedure set forth above in §6.0 and §6.1, and compared with the toxicity of strains HD1-S-1980 (the international standard of commercial BT preparations) and DIPEL 2X, a commercially available BT preparation (Abbott Laboratories, Chicago, Ill.).

TABLE XI

| | BT STRAINS HD1-19-8, HD279-72, and HD269-2-8 | | | | |
| --- | --- | --- | --- | --- | --- |
| | PLC$_{50}$ | | | | |
| Strain | HV | HZ | SE | TN | LD |
| HD1-S-1980 | 20 | 584 | 387 | 48 | 262 |
| DIPEL 2X | 21 | 360 | 264 | 31 | 50 |
| HD279-72 | 4 | 37 | 94 | 22 | 12 |
| HD1-19-8 | — | 104 | 25 | 29 | — |
| HD269-2-8 | 3 | 57 | 68 | 17 | — |

All data from powder samples.
HV = *Heliothis virescens*
HZ = *Heliothis zea*
SE = *Spodoptera exigua*
TN = *Trichoplusia ni*
LD = *Lymantria dispar*
PLC50 is in nanograms of preparation/600 mm$^2$ of diet surface.

These results show that these novel strains have generally improved toxicity relative to the known strain and the commercial preparation.

7. DEPOSIT OF MICROORGANISMS

It is within the scope of this invention that both sporulating and nonsporulating forms of the isolated strains of BT microorganisms are encompassed herein. Exemplary of the microorganisms useful in the compositions and methods disclosed herein are the following *Bacillus thuringiensis* strains which have been deposited with the Agricultural Research Culture Collection (NRRL), an International Depository located at 1815 N. University Street, Peoria, Ill. 61604 and which have been assigned the listed accession numbers:

| *B. thuringiensis* strain | Accession Numbers | Date of Deposit |
| --- | --- | --- |
| HD263-4-1 | B-18205 | April 23, 1987 |
| HD263-4-5A | B-18206 | April 23, 1987 |
| HD269-2 | B-18207 | April 23, 1987 |
| HD269-2-7 | B-18208 | April 23, 1987 |
| HD269-2-30 | B-18209 | April 23, 1987 |
| HD269-2-8 | B-18346 | March 15, 1988 |
| HD279-72 | B-18345 | March 15, 1988 |
| HD1-19-8 | B-18347 | March 15, 1988 |
| HD73-26 | B-18508 | June 12, 1989 |

Aspects of the present invention are not to be limited in scope by the microorganisms deposited, since the deposited embodiments are intended as individual illustrations. Indeed, various modifications of the invention in addition to those shown and described herein will become apparent to those skilled in the art from the foregoing description and accompanying drawings.

We claim:

1. A *Bacillus thuringiensis* bacterium deposited with NRRL and assigned Accession No. B-18205, or a mutant thereof with all the identifying characteristics of NRRL Accession No. B-18205.

2. A *Bacillus thuringiensis* bacterium deposited with NRRL and assigned Accession No. B-18206, or a mutant thereof with all the identifying characteristics of NRRL Accession No. B-18206.

3. A *Bacillus thuringiensis* bacterium deposited with NRRL and assigned Accession No. B-18207, or a mutant thereof with all the identifying characteristics of NRRL Accession No. B-18207.

4. *Bacillus thuringiensis* bacterium deposited with NRRL and assigned Accession No. B-18208, or a mutant thereof with all the identifying characteristics of NRRL Accession No. B-18208.

5. A *Bacillus thuringiensis* bacterium deposited with NRRL and assigned Accession No. B-18209, or a mutant thereof with all the identifying characteristics of NRRL accession No. B-18209.

6. A *Bacillus thuringiensis* bacterium deposited with NRRL and assigned Accession No. B-18345, or a mutant thereof with all the identifying characteristics of NRRL Accession No. B-18345.

7. A *Bacillus thuringiensis* bacterium deposited with NRRL and assigned Accession No. B-18346, or a mutant thereof with all the identifying characteristics of NRRL Accession No. B-18346.

8. A *Bacillus thuringiensis* bacterium deposited with NRRL and assigned Accession No. B-18347, or a mutant thereof with all the identifying characteristics of NRRL Accession No. B-18347.

9. An insecticide suitable for use against Lepidoptera comprising a mixture of a *Bacillus thuringiensis* of any one of claims 1, 2, 3, 4, 5, 6, 7 or 8 and a suitable carrier.

* * * * *